United States Patent [19]

Harris

[11] 4,040,968
[45] Aug. 9, 1977

[54] KETOHETEROBICYCLIC GREASE THICKENERS

[75] Inventor: Howard A. Harris, New York, N.Y.

[73] Assignee: Shell Oil Company, Houston, Tex.

[21] Appl. No.: 716,614

[22] Filed: Aug. 23, 1976

[51] Int. Cl.² .................. C10M 1/32; C10M 3/26; C10M 5/20; C10M 7/30
[52] U.S. Cl. ............................................. 252/51.5 A
[58] Field of Search ................................. 252/51.5 A

[56] References Cited

U.S. PATENT DOCUMENTS

| | | | |
|---|---|---|---|
| 2,710,839 | 6/1955 | Sivakon et al. | 252/51.5 A |
| 3,102,860 | 9/1963 | Zakin | 252/51.5 A |
| 3,324,031 | 6/1967 | Hotten | 252/51.5 A |
| 3,752,765 | 8/1973 | Birke | 252/51.5 A |

*Primary Examiner*—Delbert E. Gantz
*Assistant Examiner*—Irving Vaughn

[57] ABSTRACT

Novel Benzimidazo [2,1-a]benz[de] isoquinoline-7-one mono-urea compounds having the structure formula:

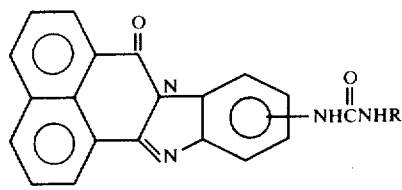

wherein R is a hydrocarbyl radical of 16-22 carbon atoms, are excellent thickening agents for grease compositions employed in high temperature applications.

5 Claims, No Drawings

KETOHETEROBICYCLIC GREASE THICKENERS

BACKGROUND OF THE INVENTION

The present invention relates to a novel class of ketoheterocyclic urea grease thickening agents for high temperature applications and to the novel grease compositions gelled therewith.

Grease compositions capable of providing effective lubrication at high temperature e.g., temperature of 300° F to 400° F, and above, have become increasingly important and numerous thickening agents have been proposed for use in such greases, e.g., soap base thickeners, inorganic clay thickeners and organic thickeners. Examples of the organic thickening agents include various polyureas, ureido compounds, amido compounds and the like. Such organic thickening agents are typically prepared by reacting one or more mono-, di- or polyamides with one or more mono-, di-, or polyicocyanates. The thickeners of this type generally produce greases having desirably high dropping points; however, they have frequently been found to have less than desirable properties in other important aspects, e.g., thermal and mechanical stability, high temperature bearing performance, oxidation and corrosion resistance, etc. The present invention provides a novel class of ketoheterocycle thickening agents which produce greases not only having desirable high dropping points but also excellent overall balance of properties.

SUMMARY OF THE INVENTION

It has now been found that grease composition with excellent high temperature lubricating properties can be produced by incorporating into a lubricating oil base vehicle a thickening agent having the formula:

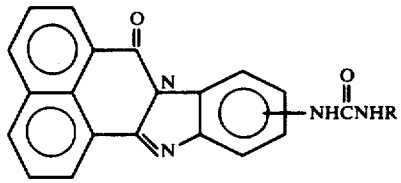

wherein R is a hydrocarbyl radical of 16–22 carbon atoms in an amount sufficient to thicken the base vehicle to grease consistency.

The grease compositions containing the novel grease thickening agents of the invention have outstanding mechanical and thermal stability in addition to the high dropping points for high temperature applications. These excellent overall qualities are believed attributable to the unique ketoheterocyclic structure of the thickening agents.

DESCRIPTION OF THE PREFERRED EMBODIMENTS

The present invention is directed to a novel class of grease thickening agents having the formula:

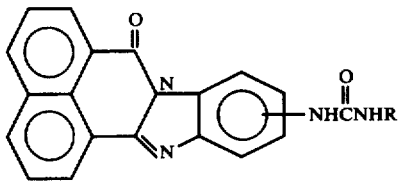

wherein R is a hydrocarbyl radical of 16–22 carbon atoms. Preferably, the hydrocarbyl radical is a straight-chain or branched-chain, saturated or unsaturated aliphatic radical. Most preferably R is a straight-chain alkyl, e.g. hexadecyl, heptadecyl, octadecyl, etc. The urea substituent is preferred to be on the tenth position of the heterobicyclic ring structure according to the ring numbering system as indicated in "The Ring Index," by Patterson, Capell and Walker (2nd ed.).

Exemplary species of the compounds of the invention include:

| | |
|---|---|
| 10-hexadecylureido-benzimidazo | [2,1-a]benz[de] isoquinoline-7-one; |
| 10-octadecylureido-benzimidazo | [2,1-a]benz[de] isoquinoline-7-one; |
| 10-eicosylureido-benzimidazo | [2,1-a]benz[de] isoquinoline-7-one. |

The benzimidazo [2,1-a]benz[de] isoquinoline-7-one mono-urea grease thickening agents of the invention can be conveniently prepared by the sequential processes of (1) refluxing naphthalic anhydride and a nitrophenylene diamine in acetic acid for about 8 to 10 hours, (2) reducing the nitro-benzimidazo [2,1-a]benz[de] isoquinoline-7-one produced with sodium sulfide, and (3) further reacting the amine product with an equivalent of the desired isocyanate in tetrahydrofuran for about 48–72 hours. The procedure or reaction sequence is illustrated by the following equations:

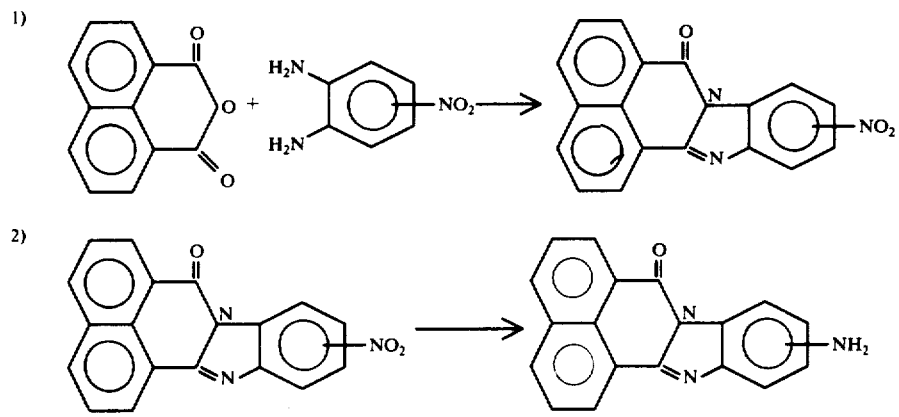

3)

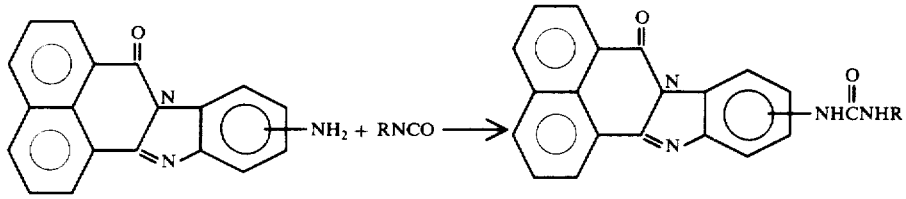

wherein R is a hydrocarbyl radical as previously defined.

This reaction sequence can be carried out in situ by adding the reactants in the lubricating oil base vehicle in the sequence described. Preferably, the ketoheterocyclic urea thickeners of the invention are prepared in the absence of the base vehicle and then incorporated into base oil. The mixing of the thickeners and the oil base vehicle may be accomplished according to conventional method by grinding the grease thickeners to a fine powder, adding the fine powder to the base oil with agitation at elevated temperature, e.g. slow heating from ambient to 150° C and then milling and baking the mixture to form a smooth grease at high temperature, e.g. 150° C.

Suitable hydrocarbylisocyanates employed in preparing the benzimidazo [2,1-a]benz[de]isoquinoline-7-one mono-urea thickening agents of the invention include saturated or unsaturated aliphatic hydrocarbylisocyanates of 16-22 carbon atoms. Preferably, the hydrocarbylisocyanates are alkylisocyanates such as hexadecylisocyanate, heptadecylisocyanate, nonadecylisocyanate, eicosylisocyanate, and docosylisocyanate. Certain of the alkylisocyanate reactants are available from commercial sources; others can be conveniently prepared by reacting the corresponding amine hydrochloride with phosgene.

The thickening agents of the invention are generally employed in grease compositions in an amount sufficient to get the oleaginous base vehicle to grease consistency. This amount can vary, for example, from about 5-50% by weight of the total composition. Normally, however, with the good thickening efficiencies of the novel grease thickening agents of this invention, thickener concentrations of 10-35% by weight are sufficient to impart the desired consistency to the base oil vehicle.

A wide variety of lubricating oils may be employed as the base vehicle in the present composition. Suitable base oils include mineral lubricating oils such as naphthenic base, paraffin base or mixed base oils having a viscosity in the range of from 50 SSU at 100° F to 300 SSU at 210° F; synthetic hydrocarbon oils such as oligomerized alpha-olefins and oils derived from coal products; synthetic oils such as alkylene polymers, alkylene oxide-type polymers, polyalkene glycols, polyethers, phosphate esters, dicarboxylic acid esters and pentaerythritol esters. The above oils may be used individually or in mixtures thereof, wherever miscible or made so by the use of solvents. Of the aforementioned base oils, mineral lubricating oils having viscosities of from about 400 to 700 SSU at 100° F are especially preferred.

In addition to the ketoheterocyclic mono-urea grease thickeners, the grease compositions of the present invention can also contain anti-corrosion additives such as disodium sebacate, glyceryl monooleate, sodium sulfonates, sodium nitrite, amino- and benzo-triazoles, and isostearamides or imidazolines of tetraethylenepentamines; oxidation inhibitors such as phenylalpha-naphthylamine, phenyl-beta-naphthylamine, diphenylamines, phenothiazine, dithiocarbamates, and various analogs and homologs thereof; viscosity index improvers such as methacrylate polymers and copolymers; extreme pressure agents, and any other additive recognized in the art to perform a particular function or functions.

The following examples illustrate the method of preparation of the thickeners of the present invention and their excellent properties in grease composition.

ILLUSTRATIVE EMBODIMENT I

Preparation of 10-octadecylureido-benzimidazo[2,1-a]benz[de]isoquinoline-7-one.

A 15.8 g portion of naphthalic anhydride was mixed with 12.2 g of 4-nitrophenylenediamine and placed in 200 ml of glacial acetic acid in a 500 ml flask. The mixture was stirred with with a magnetic stirring bar and brought to reflux. The mixture was refluxed for about eight hours and then cooled. The mixture was filtered and the insoluble product washed with ether to remove most of the acetic acid. The product was placed in the vacuum oven overnight to remove last traces of solvent. Yield was 20.6 g of 10-nitro-benzimidazo[2,1-a]benz[de]isoquinoline-7-one.

A 22.1 g portion of the 10-nitro-benzimidazo[2,1-a]benz[de]isoquinoline-7-one was placed in a 1 liter flask containing 700 ml of water and 25 g of sodium sulfide nonahydrate. The mixture was brought to reflux and refluxed for about one hour. A second 25 g portion of sodium sulfide was added. The mixture was refluxed for additional two hours, cooled, and filtered. The insoluble product was thoroughly washed with water and then dried in the vacuum oven. The yield was 18.2 g of 10-amino-benzimidazo[2,1-a]benz[de]isoquinoline-7-one.

A 5.7 g portion of the 10-amino-benzimidazo[2,1-a]benz[de]isoquinoline-7-one was added to 200 ml of distilled tetrahydrofuran in a 500 ml flask. To this mixture was added 5.9 g of Mondur O (octadecyl isocyanate) and 0.3 g of 1,4-diazobicyclo-octane. The mixture was stirred with a magnetic stirring bar and brought to reflux. The mixture was refluxed until no isocyanate peak was visible at 2240 cm$^{-1}$ on infrared spectraphotometric analysis (~48-72 hours). It was then cooled and the solvent removed on the rotary evaporator. The solid thus obtained was ground to a fine powder, stirred in either, filtered and dried in the vacuum oven. The yield was 10.7 g of 10 octadecylureido benzimidazo[2,1-a]benz[de]isoquinoline-7-one.

stability at high temperatures and the results are presented in the following table.

TABLE 1
THICKENER STRUCTURAL FORMULA

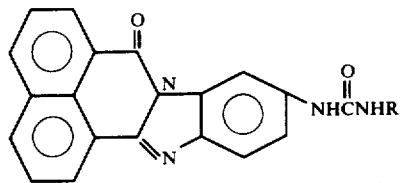

| Thickener Composition | R = $C_{18}H_{37}$ | R = $C_{19}H_{38}$(Ave) | R = $C_{21}H_{43}$(Ave) |
|---|---|---|---|
| Penetration at 0 and 60 strokes[d] | | | |
| 15% Thickener | 230/257 | 212/234 | 197/219 |
| 11% Thickener | — | — | 245/272 |
| Drop Point, ° F | 570 | 560 | 560 |
| Worked Stability[d] (% thickener) | (13) | (12.5) | (11) |
| Penetration at 0 strokes | 278 | 260 | 260 |
| Penetration at 60 strokes | 302 | 294 | 290 |
| Penetration at 1,000 strokes | 332 | 320 | 320 |
| Penetration at 10,000 strokes | 347 | 342 | 346 |
| Penetration at 100,000 strokes | 350 | 354 | 369 |
| Change from 60 to 100,000 strokes | +48 | +60 | +79 |
| Roll Test at Room Temperature, Hours | >500 | 336 | 24 |
| Penetration at 500 Hours | 86 | — | — |
| Cone Bleed at 350° F, % | 2 | 2.9 | 5.1 |
| 350° F Pope Bearing Life,[g] Hours | | | |
| Additive Package A[a] | 405[c] | 616[c] | 285[c] |
| Additive Package B[b] | 605[c] | 530[c] | 412[c] |
| 312° F Navy Bearing Life,[e] Hours | | | |
| Additive Package A | 2040[c] | | |
| 325° F-B Bearing Rig Life,[f] Hours | | | |
| Additive Package A | 142 | | |
| Additive Package B | 212 | | |

[a]1% Irganox LO-6, 1% Irganox LO-4, 1% sodium sebacate.
[b]1.5% Vanlube 81, 1% Irganox LO-6, 1% sodium sebacate.
[c]Average of at least two runs.
[d]All penetrations were determined as ¼ scale and are converted to full scale via correlation chart.
[e]204K Bearing 10M rpm 10 lb axial load, 3 lb radial load, continuous running.
[f]204K Bearing 10M rpm 100 lb radial load, continuous running.
[g]204S-17 Bearing 10M rpm 15 lb radial load, cyclic operation Note:
Base Oil employed in all formulations was a mineral lubricating oil having a viscosity of 70 SSU at 210° F. Thickener where R = $C_{18}H_{37}$ derived from octadecylisocyanate. Thickener where R = $C_{19}H_{39}$ Ave. derived from mixture of alkyl isocyanates having an average alkyl chain length of 19 carbon atoms which, in turn, were prepared via phosgenation of kemamine 150D (Humko Chemical Co.) consisting of 20% $C_{16}$, 30% $C_{18}$, 25% $C_{20}$, and 25% $C_{22}$ amines. Thickener where R = $C_{21}H_{43}$ Ave. derived from mixture of alkyl isocyanates having an average alkyl chain length of 21 carbon atoms which, in turn, were prepared via phosgenation of kemamine 150D (Humko Chemical Co.) consisting of 20% $C_{16}$, 30% $C_{18}$, 25% $C_{20}$, and 25% $C_{22}$ amines. Thickener where R = $C_{21}H_{43}$ Ave. derived from mixture of alkyl isocyanates having an average alkyl chain length of 21 carbon atoms which, in turn, were prepared via phosgenation of kemamine 190D (Humko Chemical Co.) consisting of 10% $C_{18}$, 45% $C_{20}$, and 45% $C_{22}$ amines.

ILLUSTRATIVE EMBODIMENT II

A thickened grease composition according to the invention was prepared from the product of Illustrative Embodiment I and an HVI 70/210 Neutral oil (mineral lubricating oil having a viscosity of 70 SSU at 210°). To prepare this grease composition, 55.0 g of the 10-octadecylureido-benzimido[2,1-a]benz[de]isoquinoline-7-one was ground to a fine powder with a mortar and pestle and stirred into 445.0 g of the base oil while slowly heating to 150° C. This warmed slurry was milled on a three-roll paint mill (three passes being sufficient to produce a homogenous grease) and baked in an oven for about one hour at 150° C. The baked grease was cooled to about 90° C and milled again at 150° C through the three-roll paint mill to afford a smooth grease having an ASTM dropping point of 570° F and an ASTM worked penetration (D 217) (60 strokes) of 302.

ILLUSTRATIVE EMBODIMENT III

A series of grease compositions containing various 10-alkylureido benzimidazo[2,1-a]benz[de]isoquinoline-7-one thickening agents of the invention were prepared according to the procedure in Illustrative Embodiment II. These products and the grease composition of Illustrative Embodiment II were tested for their mechanical

I claim as my invention:

1. A grease composition consisting essentially of a major account of a lubricating oil base vehicle and in an amount sufficient to thicken the base vehicle to grease consistency, a ketoheterobicyclic compound defined by the formula:

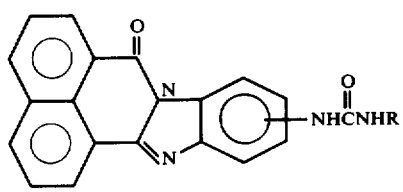

wherein R is an aliphatic hydrocarbyl radical of 16 to 22 carbon atoms.

2. The composition according to claim 1, wherein the ureido substituent is on the tenth position of the ketoheterobicyclic ring.

3. The composition according to claim 2, wherein R is selected from the class consisting of straight-chain and branched-chain alkyl radicals.

4. A composition according to claim 2, wherein R is a straight-chain alkyl of 16-22 carbon atoms.

5. The composition according to claim 1, wherein the ketoheterobicyclic compound is present in the amount of 5 50% by weight of the total composition.

* * * * *